(12) United States Patent
Young

(10) Patent No.: US 6,416,790 B1
(45) Date of Patent: Jul. 9, 2002

(54) BACTERICIDAL CONCENTRATE AND METHOD FOR TREATING BURNS AND DERMAL LESIONS

(75) Inventor: John D. Young, Seminole, FL (US)

(73) Assignee: Aqua Med, Inc., Seminole, FL (US)

( * ) Notice: Subject to any disclaimer, the term of this patent is extended or adjusted under 35 U.S.C. 154(b) by 0 days.

(21) Appl. No.: 09/524,493

(22) Filed: Mar. 13, 2000

(51) Int. Cl.⁷ .............................. A61K 9/00; A61K 9/08; A61K 9/10; A61K 9/107; A61K 9/127; A61K 33/06; A61K 33/08; A61K 33/12; A61K 33/14

(52) U.S. Cl. .................... 424/681; 424/400; 424/405; 424/450; 424/600; 424/682; 424/683; 424/684; 424/685; 424/686; 424/687; 424/688; 424/689; 424/690; 424/691; 424/692; 424/693; 424/694; 424/695; 424/696; 424/697; 424/698; 424/722; 424/DIG. 13; 514/783; 514/786; 514/858; 514/859; 514/860; 514/861; 514/862; 514/863; 514/864; 514/865; 514/886; 514/887; 514/938; 514/939; 514/964; 514/975; 422/28

(58) Field of Search ............................... 424/400, 450, 424/600, 682, 683–698, 405, 681, 722, DIG. 13; 514/783, 786, 858–865, 886, 887, 938, 939, 964, 975; 422/28

(56) References Cited

U.S. PATENT DOCUMENTS 3,893,943 A * 7/1975 Willard, Sr. ................. 502/168
4,029,770 A * 6/1977 Willard, Sr. ................. 424/127

OTHER PUBLICATIONS

Werner, C., "McFarland O.5 turbidity standard" in: http://gold.aecom.yu.edu/id/micro/mcfarland.htm, Apr. 1999.*

Biosis abstract, accession No. 1997:397110, 1997.*

* cited by examiner

Primary Examiner—John Pak
(74) Attorney, Agent, or Firm—Larson & Larson, PA; James E. Larson

(57) ABSTRACT

The concentrate is a liquid mixture of about 1000 parts by volume of ultra pure water having an electrical resistance of 16–26 megohms, total dissolved solids of less than 0.04 parts per million and a specific conductance of less than 0.10 microhmo to about 1.2 to 3 parts by volume of Willard Water as prepared in accordance with U.S. Pat. No. 3,893,943. The liquid concentrate is applied directly to a skin surface area having a burn or other dermal lesion to protect the area from bacterial contamination.

8 Claims, No Drawings

BACTERICIDAL CONCENTRATE AND METHOD FOR TREATING BURNS AND DERMAL LESIONS

FIELD OF THE INVENTION

This invention relates to a catalyst called Willard Water. More particularly, it refers to a bactericidal concentrate formed from a mixture of the catalyst and ultra pure water and the use of the bactericidal concentrate to treat burns and dermal lesions.

BACKGROUND OF THE INVENTION

Willard Water is set forth in U.S. Pat. No. 3,893,943 as a novel catalyst and its preparation is therein described. Willard Water has a poor shelf life insofar as its use in a bactericidal solution. A concentrate is needed that will provide an extended shelf life and will be useful to treat epidermal body surfaces that may be contaminated with bacteria.

SUMMARY OF THE INVENTION

The present invention solves the above problem by providing a bactericidal concentrate with a liquid mixture ratio of about 1.2 to 3 ml of Willard Water to about one liter of ultra pure water having an electrical resistance of 16–26 megohms, total dissolved solids of less than 0.04 parts per million and a specific conductance of less than 0.10 microhm. The Willard Water employed in the concentrate is as described in U.S. Pat. No. 3,893,943. The concentrate is used to apply to the epidermis of patients to control bacterial contaminations. A gel for treatment of burns also can be formed from a gel formulation containing about 5.6 ml of Willard Water. The concentrate of this invention has a shelf life in a plastic container of at least two and one half years compared to a shelf life of Willard Water combined with distilled water of less than seven months.

DETAILED DESCRIPTION OF THE INVENTION

The liquid bactericidal concentrate of this invention is made from 1.2 to 3 parts by volume of Willard Water made according to the description of the catalyst described in U.S. Pat. No. 3,893,943, incorporated herein by reference, to 1000 parts by volume of ultra pure water.

The ultra pure water is made by first passing potable water through a 5 micron sediment filter and then through a granulated activated charcoal bed having a depth of about 20 cm. The water is then passed through a 1.2 cubic foot mixed bed deionizer resin such as SIBRON Model No. NM-60. The resulting treated water is passed twice through a standard reverse osmosis process utilizing Model FC-018A filters obtained from Water Link Technologies, Inc. and then through a 0.2 micron filter to obtain ultra pure water having an electrical resistance of 16–26 megohms, total dissolved solids of less than 0.04 parts per million and a specific conductance of less than 0.10 micromho.

The ultra pure water is mixed in a holding drum with the Willard Water at varying ratios of 1000 to 1.2–3 parts by volume depending upon the bacteria for which control is sought.

About 1.2 ml of Willard Water is added to one liter of the ultra pure water to create a liquid mixture for treatment of Staphylococcus. Streptococcus, E. coli and Pseudomonas bacteria. In treating burns with a liquid, 2.8 ml of Willard Water is added to one liter of the ultra pure water. The solutions are buffered to a pH of 8.0 to 8.5.

For further treatment of burn victims, a gel is formed containing 5.8 ml of Willard Water in 1000 ml of a gel formulation. The gel formulation will contain sodium, silicate, sulfate of ester of oil of Euphorbiaceae, magnesium, calcium, chloride, glycerin, xanthin gum, methanol, paraben, potassium sorbate and sodium benzoate. The gel formulation should be buffered to a pH of 8.0 to 8.5.

Either the liquid concentrate or gel concentrate is applied directly to a patient's skin surface containing a burn or other lesion. The burn or lesion begins healing within a few days without being affected by bacterial contamination.

COMPARATIVE EXAMPLES

A double blind study was carried out to compare the shelf life of Willard Water concentrate in 1000 ml distilled water (concentrate A) with a Willard Water concentrate containing 1.2 ml of Willard Water to 1000 ml of ultra pure water (concentrate B). A quantity of each of the concentrates had been stored for three years in 8 oz. plastic bottles.

Concentrate A

The liquid formulation contained in the 8 oz. bottle was applied to a filter paper which was smeared with Staphylococcus aureus in a neutral agar and tested in accordance with a 0.5 McFarland standard. No effect was noted in the Staphylococcus aureus growing on the filter paper.

Concentrate B

The liquid formulation contained in the 8 oz. bottle was applied to a filter paper which was smeared with Staphylococcus aureus in a neutral agar and tested in accordance with a 0.5 McFarland standard. The Staphylococcus aureus did not grow on the filter paper and was sensitive to the formulation on the filter paper.

The above description has described specific formulations prepared according to the teachings of this invention. The inventive concept is not limited to the higher range of Willard Water to ultra pure water but includes equivalents that can be formulated without causing injury to the patient.

Having thus described the invention what is claimed and desired to be secured by Letters Patent is:

1. A bactericidal concentrate comprising:
   (a) a liquid mixture ratio of about 1000 parts by volume ultra pure water having an electrical resistance of 16–26 megohms, total dissolved solids of less than 0.04 parts per million and a specific conductance of less than 0.10 micromho to about 1.2 to 3 parts by volume of catalyst micelles prepared by admixing a water soluble alkali metal silicate with an aqueous medium containing a dissolved substance which is a source of calcium ion and a dissolved substance which is a source of magnesium ion;
   the aqueous medium containing the dissolved substances in amounts to provide between about $1\times10^4$ and $1\times10^1$ mole per liter each of calcium ion and magnesium ion;
   the aqueous medium containing the dissolved substances in amounts to provide a molar ratio of calcium ion to magnesium ion between about 2.0:1.0 and 1.0: 2.0;
   reacting the alkali metal silicate with the dissolved substances providing calcium ion and magnesium ion to produce an aqueous suspension of finely divided particles of the reaction product;
   admixing a micelle-forming surfactant with the aqueous medium in an amount to form catalyst micelles comprising the finely divided particles of the reaction product upon agitating the aqueous medium; and agitating the aqueous medium containing the finely divided particles of the reaction product and surfactant to form the catalyst micelles.

2. The bactericidal concentrate according to claim 1 wherein the source of calcium ion is calcium chloride and the source of magnesium ion is magnesium chloride or magnesium sulfate.

3. The bactericidal concentrate according to claim 1 wherein the surfactant employed is castor oil.

4. Method of treating a burned area of skin comprising applying a concentrate according to claim 1 to the burned area.

5. Method of treating a skin lesion comprising applying a concentrate according to claim 1 to the skin lesion.

6. A bacterieial concentrate comprising 1000 parts by volume of ultra pure water having an electrical resistance of 16–26 megohms, total dissolved solids of less than 0.04 parts per million and a specific conductance of less than 0.10 micromho to 1.2 to 3 parts by volume of catalyst micelles prepared by admixing a sodium metasilicate with an aqueous medium containing a dissolved substance which is a source of calcium ions and a dissolved substance which is a source of magnesium ions, the aqueous medium containing the dissolved substances in amounts to provide between about $1 \times 10^4$ to $1 \times 10^1$ mole per liter each of calcium and magnesium ion, resulting in a molar ratio of calcium ion to magnesium ion between 2.0:1.0 and 1.0:2.0 and further adding a micelle-forming surfactant.

7. Method of treating a skin lesion comprising applying a concentrate according to claim to the skin lesion.

8. Method of treating a burned area on a patient's skin comprising applying a liquid concentrate according to claim 6 to the burned area.

* * * * *

UNITED STATES PATENT AND TRADEMARK OFFICE
CERTIFICATE OF CORRECTION

PATENT NO. : 6,416,790 B1  Page 1 of 1
DATED : July 9, 2002
INVENTOR(S) : John D. Young It is certified that error appears in the above-identified patent and that said Letters Patent is hereby corrected as shown below:

Column 2,
Line 54, replace "$1 \times 10^4$ and $1 \times 10^{1}$" with -- $1 \times 10^{-4}$ and $1 \times 10^{-1}$ --.

Column 4,
Line 7, replace "$1 \times 10^4$ and $1 \times 10^{1}$" with -- $1 \times 10^{-4}$ and $1 \times 10^{-1}$ --.

Signed and Sealed this

Fifteenth Day of October, 2002

Attest:

JAMES E. ROGAN
Attesting Officer  Director of the United States Patent and Trademark Office